(12) United States Patent
Waters et al.

(10) Patent No.: US 9,782,148 B2
(45) Date of Patent: Oct. 10, 2017

(54) CATHETERS FOR IMAGING AND ABLATING TISSUE

(71) Applicant: ACIST MEDICAL SYSTEMS INC., Eden Prairie, MN (US)

(72) Inventors: Kendall R. Waters, Livermore, CA (US); Thomas C. Moore, Livermore, CA (US); Robert Zelenka, Milpitas, CA (US); Richard Bautista, Palo Alto, CA (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 154 days.

(21) Appl. No.: 13/687,801

(22) Filed: Nov. 28, 2012

(65) Prior Publication Data
US 2013/0137980 A1 May 30, 2013

Related U.S. Application Data

(60) Provisional application No. 61/563,935, filed on Nov. 28, 2011.

(51) Int. Cl.
*A61B 8/12* (2006.01)
*A61B 18/18* (2006.01)
(Continued)

(52) U.S. Cl.
CPC ........... *A61B 8/12* (2013.01); *A61B 8/445* (2013.01); *A61B 18/1492* (2013.01);
(Continued)

(58) Field of Classification Search
CPC ....... A61B 8/12; A61B 8/4461; A61B 8/4466; A61B 18/18; A61B 18/1492;
(Continued)

(56) References Cited

U.S. PATENT DOCUMENTS 5,409,000 A 4/1995 Imran
5,454,809 A * 10/1995 Janssen .................. A61B 18/12
600/439

(Continued)

FOREIGN PATENT DOCUMENTS

CN 1942145 A 4/2007
CN 101902972 A 12/2010
(Continued)

OTHER PUBLICATIONS

International Search Report, dated Mar. 25, 2013 for PCT/US2012/066840, from which the instant application is based, 17 pages.
(Continued)

*Primary Examiner* — Long V Le
*Assistant Examiner* — Don N Ho
(74) *Attorney, Agent, or Firm* — Fredrickson & Byron, P.A.

(57) ABSTRACT

An ultrasound catheter includes an elongated body, a first and second ablation element each configured to ablate soft tissue and an imaging core having an ultrasound transducer. In another example, an ultrasound catheter includes an elongated body, a RF ablator configured to ablate soft tissue at a frequency less than 1 MHz, and an ultrasound transducer configured to image at a frequency greater than or equal to 10 MHz. In another example, an ultrasound catheter apparatus includes an ultrasound catheter having an ablator and an ultrasound transducer, and a graphical user interface displayed using a computer processor. The graphical user interface displays a real-time image of a treatment area and the ultrasound catheter, and a chart displaying ablation as a function of time, the chart being updated in real-time.

30 Claims, 7 Drawing Sheets

(51) Int. Cl.
*A61B 18/14* (2006.01)
*A61B 8/00* (2006.01)
*A61B 17/00* (2006.01)
*A61B 18/00* (2006.01)
*A61B 34/00* (2016.01)
*A61B 90/00* (2016.01)

(52) U.S. Cl.
CPC .... *A61B 18/18* (2013.01); *A61B 2017/00318* (2013.01); *A61B 2018/00577* (2013.01); *A61B 2018/00982* (2013.01); *A61B 2034/254* (2016.02); *A61B 2090/3784* (2016.02); *A61B 2218/002* (2013.01)

(58) Field of Classification Search
CPC .............. A61B 2019/528; A61B 8/445; A61B 2218/002; A61B 2017/00318; A61B 2018/00577; A61B 2018/00982; A61B 2019/564
USPC ........ 600/437, 439, 461, 462, 466, 467, 477
See application file for complete search history.

(56) References Cited

U.S. PATENT DOCUMENTS

| 5,588,432 | A | * | 12/1996 | Crowley | A61B 5/02007 600/374 |
|---|---|---|---|---|---|
| 6,245,020 | B1 | * | 6/2001 | Moore et al. | 600/466 |
| 8,317,711 | B2 | * | 11/2012 | Dala-Krishna | A61B 8/12 600/437 |
| 8,414,492 | B2 | | 4/2013 | Hadjicostis | |
| 2006/0122591 | A1 | * | 6/2006 | Keidar | 606/27 |
| 2008/0071173 | A1 | | 3/2008 | Aldrich | |
| 2009/0292209 | A1 | * | 11/2009 | Hadjicostis | A61B 5/042 600/463 |
| 2010/0057072 | A1 | | 3/2010 | Roman et al. | |
| 2011/0071513 | A1 | | 3/2011 | Shin et al. | |
| 2011/0144524 | A1 | | 6/2011 | Fish | |

FOREIGN PATENT DOCUMENTS

| JP | H06500248 | 1/1994 |
|---|---|---|
| JP | 2002500911 | 1/2002 |
| JP | 2003524499 | 8/2003 |
| JP | 2011067591 | 4/2011 |
| WO | 9937211 | 7/1999 |
| WO | 0164121 | 9/2001 |

OTHER PUBLICATIONS

First Office Action dated Aug. 27, 2015, for co-pending CN Application No. 2012800584806 filed May 28, 2014, 12 pages.
First Office Action dated Nov. 11, 2015, for co-pending JP Application No. 2014-543622 filed May 27, 2014, 13 pages.

* cited by examiner

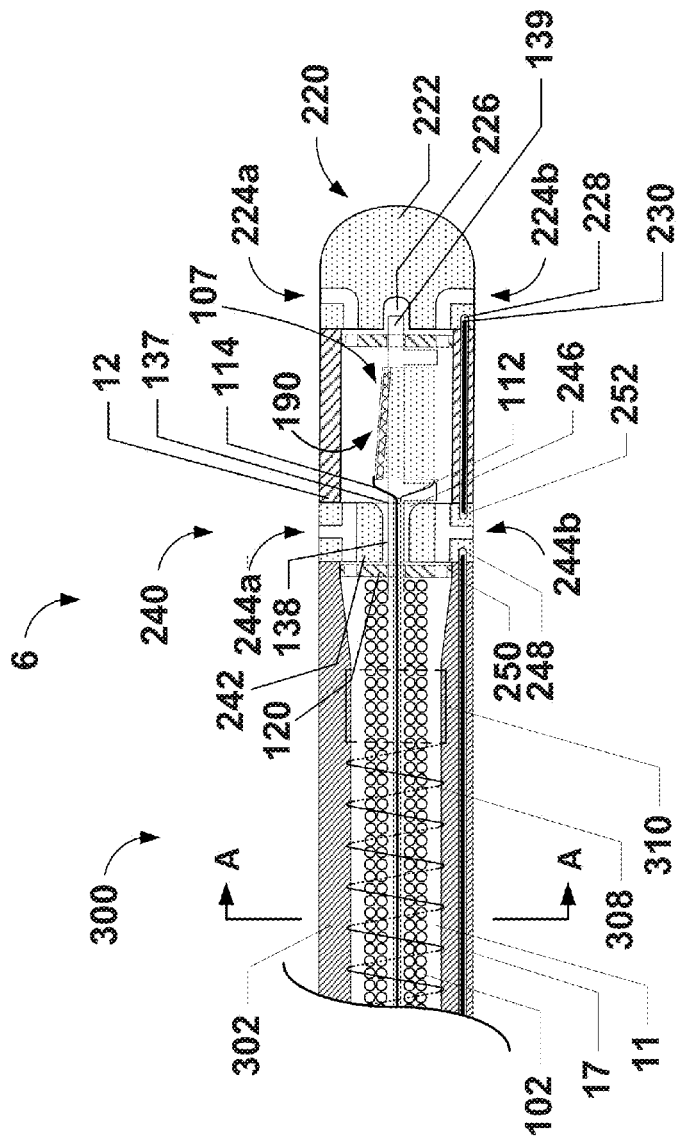
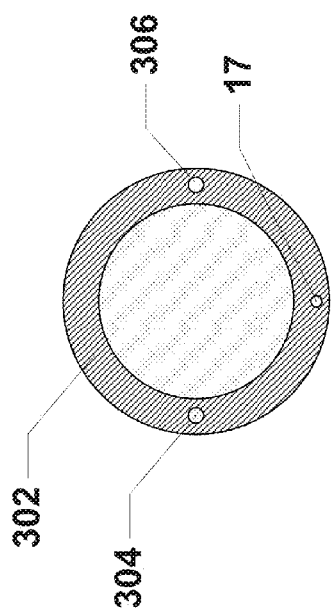
FIG. 6
FIG. 6A

CATHETERS FOR IMAGING AND ABLATING TISSUE

PRIORITY CLAIM

The present application claims the benefit of copending U.S. Provisional Patent Application Ser. No. 61/563,935, filed Nov. 28, 2011, which application is incorporated herein by reference in its entirety.

TECHNICAL FIELD

This document generally relates to ultrasound imaging catheters. The document further relates to ablation catheters having integrated imaging capabilities. The document also relates to radiofrequency (RF) ablation catheters having integrated imaging capabilities.

BACKGROUND

Radiofrequency catheter ablation may be used to treat cardiac arrhythmias. Normally, heart muscle cells are stimulated by electrical impulses originating from an area of specialized cells known as the sinus node. Electrical impulses from the sinus node move along the conduction fibers of the heart and stimulate cardiac muscle to contract in a uniform and regular manner, producing a heartbeat.

Cardiac arrhythmias may occur when other cells in the heart outside of the sinus node become active and generate abnormal electrical impulses. These abnormal impulses may compete with, or overwhelm, the impulses originating from the sinus node thereby causing cardiac muscle to contract in a non-uniform or irregular manner. Cardiac arrhythmias may also occur when abnormal pathways, or routes, form within the heart effectively short circuiting the regular pathway of the electrical impulses originating from the sinus node. In these situations, heartbeats may become irregular resulting in a cardiac arrhythmia.

Minimally invasive intracardiac RF ablation catheters for ablation of cardiac structures may be used to treat cardiac arrhythmias. RF ablation may be used to damage cardiac tissue that is generating abnormal electrical impulses or conducting electrical impulses along an abnormal pathway. The damaged tissue no longer generates or conducts electrical impulses and the normal heartbeat is restored. RF ablation in the heart may be aided by echocardiographic imaging of soft tissue, particularly cardiac structures. Image guidance of cardiac ablations can improve the safety and efficacy of the procedure.

SUMMARY

In one embodiment of this application, a RF ablation catheter may have two ablation electrodes and an ultrasound transducer. The catheter may be configured to have an imaging frequency and an ablation frequency that minimize interference to an ultrasound image. The catheter may further be electrically coupled to an imaging console which may include a graphical user interface configured to aid an individual in ablating a treatment area.

In one embodiment, an ultrasound catheter is provided. The catheter can include an elongated body having a longitudinal dimension, a distal end and an imaging core lumen. The catheter can include a first and second ablation element each configured to ablate soft tissue. The catheter can include an imaging core having an ultrasound transducer.

Such an ultrasound catheter can include a variety of characteristics. In some embodiments, the ultrasound transducer can be rotatable relative to the elongated body. In some embodiments, the imaging core can further include a mirror that can be rotatable relative to the elongated body. In such embodiments, the ultrasound transducer can be rotationally fixed relative to the elongated body. In some embodiments, the catheter can include at least one bearing that restricts longitudinal displacement of the ultrasound transducer within the elongated body. In such embodiments, the at least one bearing may be fixed to the elongated housing proximal to the ultrasound transducer. In some embodiments, the at least one bearing can include a first and second bearing that can be fixed to the elongated body. In such embodiments the first bearing can be located proximal to the ultrasound transducer and the second bearing can be located distal to the ultrasound transducer. In some embodiments the imaging core and the first and second ablation elements may be configured such that a treatment area imaged by the imaging core includes the tissue to be ablated. In some embodiments, the first and second ablation elements may be radio frequency ablation elements. In such embodiments, the first and second ablation elements comprise a first electrode and a second electrode, respectively. In some embodiments, the first and second electrodes may not be electrically coupled. In some such embodiments, the first and second electrodes may be independently controlled. In some embodiments, the ultrasound transducer can be configured to image at a frequency greater than or equal to 10 MHz and the first and second electrodes may be configured to ablate at a frequency less than or equal to 1 MHz. In such embodiments, the interference caused by the ablating frequency can be less than or equal to 50% of the power level of the imaging frequency. In some embodiments, the first and second electrodes may each comprise a solid piece of conductive material. In some embodiments, the first and second electrodes each comprise a conductive layer on the elongated body. In some embodiments, the first and second ablation elements can include at least one irrigation port. In some embodiments, the first ablation element can be proximal to the ultrasound transducer and the second ablation element can be distal to the ultrasound transducer. In some embodiments, the elongated body can further include a deflection section to enable steering of the distal end of the elongated body.

In one embodiment, an ultrasound catheter can be provided. The catheter can include an elongated body having a longitudinal dimension, a distal end and an imaging core lumen. The catheter can include a RF ablator configured to ablate soft tissue at an ablating frequency less than or equal to 1 MHz. The catheter can include an imaging core having an ultrasound transducer configured to image at an imaging frequency greater than or equal to 10 MHz, the interference caused by the ablating frequency being less than or equal to 50% of the power level of the imaging frequency.

Such an ultrasound catheter can include a variety of characteristics. In some embodiments, the imaging frequency of the ultrasound transducer can be between 10-20 MHz. In some embodiments, the imaging frequency of the ultrasound transducer can be between 20-30 MHz. In some embodiments, the imaging frequency of the ultrasound transducer can be between 30-40 MHz. In some embodiments, the imaging frequency of the ultrasound transducer can be between 40-50 MHz. In some embodiments, the imaging frequency of the ultrasound transducer can be between 50-60 MHz. In some embodiments, the interference caused by the ablating frequency can be between 40-50% of the power level of the imaging frequency. In some embodiments, the interference caused by the ablating frequency can be between 30-40% of the power level of the imaging frequency. In some embodiments, the interference caused by the ablating frequency can be between 20-30% of the power level of the imaging frequency. In some embodiments, the interference caused by the ablating frequency can be between 10-20% of the power level of the imaging frequency. In some embodiments, the interference caused by the ablating frequency can be between 1-10% of the power level of the imaging frequency. In some embodiments, the ultrasound transducer can be rotatable relative to the elongated body. In some embodiments, the imaging core can further include a mirror rotatable relative to the elongated body. In such embodiments, the ultrasound transducer may be rotationally fixed relative to the elongated body. In some embodiments, the catheter may include at least one bearing that restricts longitudinal displacement of the imaging core within the elongated body. In such embodiments, the at least one bearing may be fixed to the elongated body proximal to the ultrasound transducer. In some embodiments, the at least one bearing can include a first and second bearing fixed to the elongated body. In such embodiments, the first bearing may be located proximal to the ultrasound transducer and the second bearing may be located distal to the ultrasound transducer. In some embodiments, the imaging core and the RF ablator may be configured such that a treatment area imaged by the imaging core includes the tissue to be ablated. In some embodiments, the RF ablator may further include an electrode, the electrode comprising a solid piece of conductive material. In some embodiments, the RF ablator may further include an electrode, the electrode comprising a conductive layer on the elongated body. In some embodiments, the RF ablator may include at least one irrigation port. In some embodiments, the RF ablator can further include a first electrode proximal to the ultrasound transducer and a second electrode distal to the ultrasound transducer. In some embodiments, the elongated body can further include a deflection section to enable steering of the distal end of the elongated body.

In one embodiment, an ultrasound catheter apparatus can be provided. The catheter apparatus can include an ultrasound catheter having one ablator configured to ablate soft tissue and an ultrasound transducer. The catheter apparatus can include a graphical user interface displayed using a computer processor. The interface can include an image displaying a treatment area and the ultrasound catheter, the image being updated in real-time. The interface can include a chart displaying ablation as a function of time, the chart being updated in real-time.

Such an ultrasound catheter apparatus can include a variety of characteristics. In some embodiments, the image further displays an expected ablation region for the ultrasound catheter in the treatment area. In some embodiments, the image can display an ablation vector, the ablation vector beginning at the ultrasound catheter and extending into the treatment area. In some embodiments, ablation in the chart can be displayed as the brightness of the image along the ablation vector. In some embodiments, the chart can display the magnitude of the ablation vector. In some embodiments, the ablator can be an RF ablator. In such embodiments, the chart may display the power of the RF ablator as a function of time. In some embodiments, the graphical user interface can include a static image displaying the treatment area. In some embodiments, the graphical user interface can include selectable icons. In such embodiments, the selectable icons can be selectable by the user to control the graphical user interface and the ultrasound catheter.

BRIEF DESCRIPTION OF THE DRAWINGS

The following drawings illustrate some particular embodiments of the present invention and therefore do not limit the scope of the invention. The drawings are not to scale (unless so stated) and are intended for use in conjunction with the explanations in the following detailed description. Some embodiments will hereinafter be described in conjunction with the appended drawings, wherein like numerals denote like elements.

FIG. 6 is a sectional view of a steerable ablation catheter having integrated imaging capabilities in accordance with an embodiment.

FIG. 6A is a sectional view of the steerable ablation catheter of FIG. 6 along lines A-A of FIG. 6.

DETAILED DESCRIPTION OF THE PREFERRED EMBODIMENTS

The following detailed description is exemplary in nature and is not intended to limit the scope, applicability, or configuration of the invention in any way. Rather, the following description provides some practical illustrations for implementing some embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

For illustrative purposes only, this document provides certain examples appropriate for intracardiac ablation catheters having integrated imaging capabilities. The described examples do not limit the application of the invention only to intracardiac ablation catheter having integrated imaging capabilities.

Figure 1:
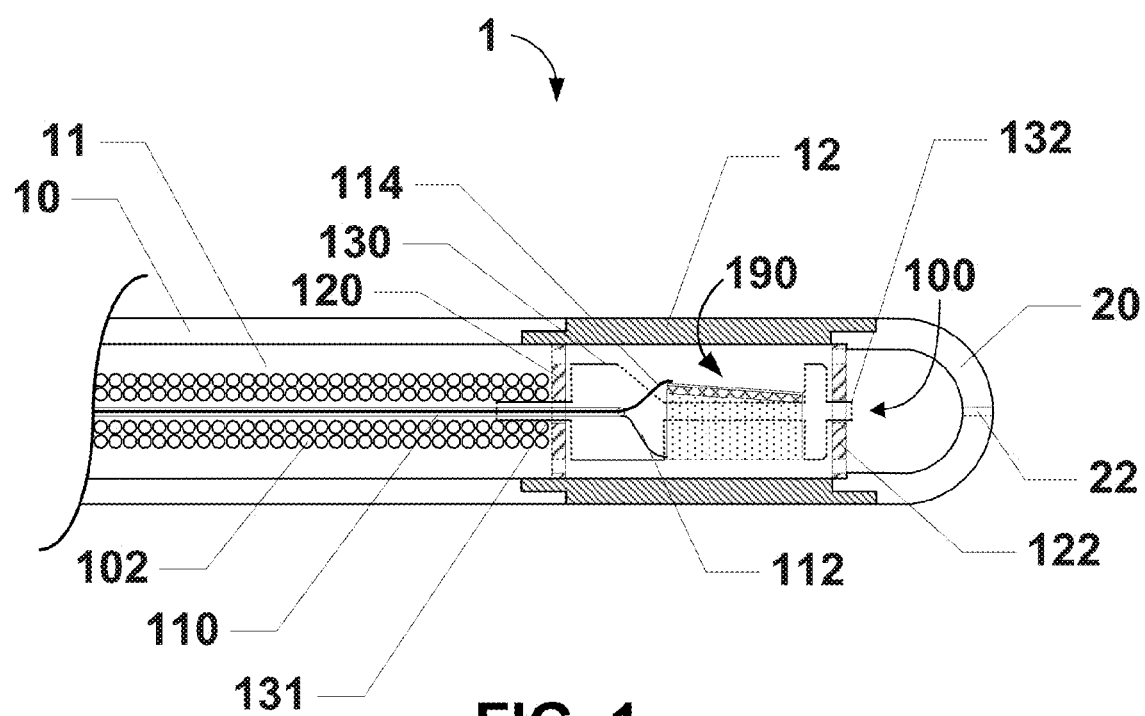
FIG. 1 is a sectional view of an imaging catheter in accordance with an embodiment.

FIG. 1 is a sectional view of an imaging catheter 1 in accordance with an embodiment. In this example, an imaging catheter 1 includes midshaft 10, imaging core lumen 11, imaging window 12, distal tip 20, proximal bearing 120, and distal bearing 122. The catheter length may be generally between 100 cm and 150 cm, more preferably between 110 cm and 120 cm. The outer diameter of midshaft 10 and imaging window 12 may be between 6 F and 10 F, as for example about 7 F. Midshaft 10 may be formed of a biocompatible flexible material such as high-density polyethylene, another thermoplastic polymer, or a reinforced polymer such as braided polyurethane. Imaging window 12 may be formed of a biocompatible flexible material such as high-density polyethylene, low-density polyethylene, a blend of high-density and low-density polyethylene, polymethylpentene, or other thermoplastic polymer that minimizes acoustic loss. Distal tip 20 may be formed of a low durometer material such as polyether block amide (Pebax®) or blend of Pebax grades such as Pebax 63D and 40D.

Imaging core lumen 11 can have a diameter of sufficient size to house imaging core 100 and may be between 0.05" and 0.125". Imaging core 100 can include torque coil 102, transmission line 110, transducer housing 130, and ultrasound transducer 190. Proximal bearing 120 and distal bearing 122 restrict the longitudinal position of transducer housing 130 and ultrasound transducer 190 with respect to imaging window 12. Proximal bearing 120 and distal bearing 122 may be formed of an ultra-high molecular weight plastic, a metal, or other polymer material such as Rulon®. Proximal bearing 120 and distal bearing 122 may be fixed in longitudinal position relative to imaging window 12 by adhesive, press fitting, or by flowing the bearings 120, 122 and the imaging window 12.

Transducer housing 130 can include proximal journal 131 and distal journal 132. Proximal journal 131 rotates within proximal bearing 120. Distal journal 132 rotates within distal bearing 122. Transducer housing 130 may be composed of a rigid material such as stainless steel. Transducer housing 130 may be machined or manufactured using a combination of laser cutting and welding. Proximal journal 131 can be bonded to torque coil 102 to enable rotation of transducer housing 130 when torque coil 102 rotates. Exemplary bonding techniques include soldering, brazing, and welding. As noted above, torque coil 102, and transducer housing 130 may be enclosed by midshaft 10 and imaging window 12, respectively. This configuration prevents trauma to the patient that would otherwise be caused by the rotation of torque coil 102 and transducer housing 130.

Imaging core 100 can be electrically and mechanically coupled to an imaging console. The electrical coupling enables sending and receiving of electrical signals along transmission line 110 to ultrasound transducer 190. The mechanical coupling enables rotation of imaging core 100. Torque coil 102 may be formed of a stainless steel roundwire coil with a coil outer diameter in the range 0.020" to 0.100". Torque coil 102 may be configured to minimize non-uniform rotation of imaging core 100. Non-uniform rotation of imaging core 100 may be minimized by aligning proximal bearing 120 and distal bearing 122 near the rotational center of imaging core 100 and fixing each bearing to the catheter.

Ultrasound transducer 190 can include at least a piezoelectric layer. Ultrasound transducer 190 may include conductive layers, at least one matching layer, and a backing layer. Ultrasound transducer 190 may include a lens. In this example, ultrasound transducer 190 can be substantially rectangular in shape, but may be configured in other shape, including square, circle, and oval in other examples. Ultrasound transducer 190 may include thin, metal electrode layers and may be formed from gold or chrome, for example, to facilitate electrical excitation of the piezoelectric layer. The ultrasound transducer generally operates over frequency ranges of 5 MHz to 60 MHz. Design and fabrication of ultrasound transducers for imaging catheters are known to those skilled in the art.

Ultrasound transducer 190 can be angled toward distal tip 20 to assist an individual in navigating imaging catheter 1. The angle of ultrasound transducer 190 can be chosen to minimize the travel path of the imaging frequency through the catheter sheath and refraction from the catheter sheath. The angle may also improve image quality by minimizing potential interference that may result from ultrasound energy passing through imaging window 12. In one example, the angle can be between 4-10 degrees relative to the catheter axis.

Transmission line 110 can be disposed within torque coil 102 and can include shield lead 112 and center conductor 114. Shield lead 112 and center conductor 114 may be coupled across ultrasound transducer 190 as shown. Transmission line 110 couples electrical energy to ultrasound transducer 190 to cause the transducer to generate a pressure field into imaging core lumen 11 of imaging window 12. Ultrasound transducer 190 may be electrically connected to a signal generator to electrically excite the transducer. The ultrasound transducer 190 may be electrically connected to a receiver to detect pressure fields that are reflected from surrounding tissue and converted to electrical signals by the transducer.

Imaging core lumen 11 can be preferably filled with a flushing fluid, such as saline. The flushing fluid flows from the proximal end of the catheter to distal tip 20 of the catheter and serves to efficiently couple ultrasonic energy into the sheath and then to the surrounding tissue. Bearings 120, 122 may have pass-through channels that facilitate flow of the flushing fluid. The flushing fluid may exit imaging catheter 1 through flushing exit port 22.

Imaging catheter 1 can include a mechanically rotating ultrasound transducer 190 that can be fixed in longitudinal position with respect to imaging window 12. An imaging catheter having an ultrasound transducer fixed in longitudinal position ensures that the ultrasound transducer images at substantially the same longitudinal position with respect to the catheter regardless of the tortuosity of the access route for delivery of the imaging catheter to the anatomical site of interest, such as a heart chamber.

Figure 2:
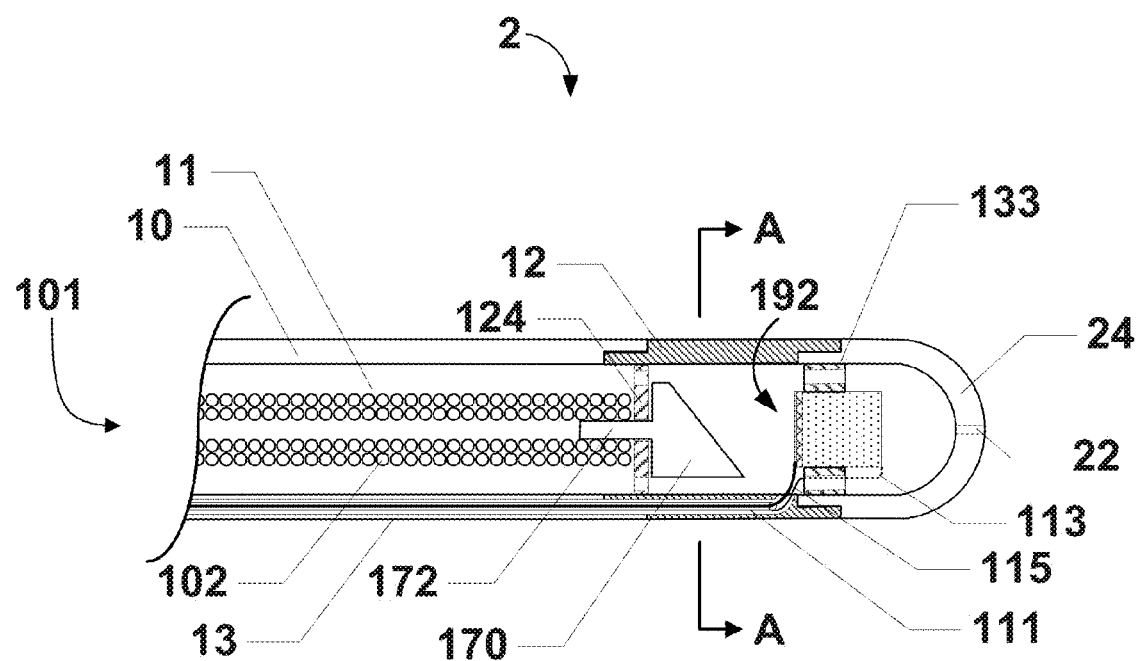
FIG. 2 is a sectional view an imaging catheter in accordance with an embodiment.
Figure 2A:
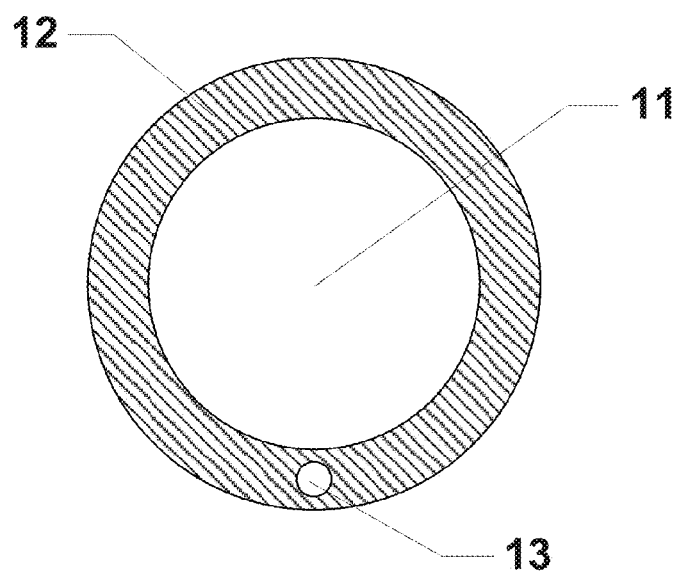
FIG. 2A is a sectional view of the imaging catheter of FIG. 2 along lines A-A.

FIGS. 2 and 2A are sectional views of an imaging catheter 2 in accordance with an embodiment. Imaging catheter 2 can include midshaft 10, imaging core lumen 11, imaging window 12, transmission line lumen 13, distal tip 24, and bearing 124. Imaging catheter 2 can include imaging core 101 wherein imaging core 101 can include torque coil 102, transmission line 111, transducer housing 133, rotating mirror 170, and ultrasound transducer 192.

Ultrasound transducer 192 can be fixed in position with respect to imaging window 12 by transducer housing 133. Transducer housing 133 may be formed of an ultra-high molecular weight plastic, a metal, or an epoxy. Transducer housing 133 may be fixed in longitudinal position relative to imaging window 12 by adhesive, press fitting, or by flowing transducer housing 133 and distal tip 24.

Transmission line 111 can be substantially disposed within transmission line lumen 13 and can include shield lead 113 and center conductor 115. Shield lead 113 and a center conductor 115 may be coupled across ultrasound transducer 192 as shown. Transmission line 111 couples electrical energy to the transducer to cause ultrasound transducer 192 to generate a pressure field into imaging core lumen 11 of imaging window 12. The pressure wave can be directed outside of imaging catheter 2 into surrounding tissue by rotating mirror 170.

Rotating mirror 170 may be composed of a material of high acoustic impedance and high reflectivity, such as polished stainless steel. Rotating mirror 170 may have a planar face as illustrated and may have a shaped face that enables focusing of the pressure field generated by ultrasound transducer 192. Rotating mirror 170 can include journal 172. Rotating mirror 170 and journal 172 may be machined or be manufactured using a combination of machining and bonding. Journal 172 can be bonded to torque coil 102 to enable rotation of rotating mirror 170 when torque coil 102 rotates. Exemplary bonding techniques include soldering, brazing, and welding. As noted above, torque coil 102, and rotating mirror 170 may be enclosed by midshaft 10 and imaging window 12, respectively. This configuration prevents trauma to the patient that would otherwise be caused by the rotation of torque coil 102 and rotating mirror 170.

Rotating mirror 170 can be angled to direct ultrasound energy emitted by ultrasound transducer 192 outwardly into the relevant tissue. The imaging area of ultrasound transducer 192 can be angled toward distal tip 24 to assist an individual in navigating a catheter. The angle at which rotating mirror 170 directs ultrasound energy can be chosen to minimize the travel path of the imaging frequency through the catheter sheath and refraction from the catheter sheath. The angle may also improve image quality by minimizing potential interference that may result from ultrasound energy passing through imaging window 12. In one example, the angle at which rotating mirror 170 may direct ultrasound energy can be between 4-10 degrees relative to the catheter axis.

Journal 172 may rotate within bearing 124. Bearing 124 restricts the longitudinal position of rotating mirror 170 with respect to imaging window 12. Bearing 124 may be formed of an ultra-high molecular weight plastic, a metal, or other polymer material such as Rulon®. Bearing 124 may be fixed in longitudinal position relative to imaging window 12 by adhesive, press fitting, or by flowing bearing 124 and imaging window 12.

Imaging catheter 2 can include an imaging core having an ultrasound transducer and a mechanically rotating mirror that may be fixed in longitudinal position with respect to the imaging window. An imaging catheter having a rotating mirror fixed in longitudinal position ensures that the imaging core images at substantially the same longitudinal position with respect to the catheter regardless of the tortuosity of the access route for the delivery of the imaging catheter. Further, having a non-rotating ultrasound transducer avoids having to couple a non-rotating system to a rotating transducer.

A catheter having a fixed imaging plane as illustrated in FIGS. 1, 2, and 2A may be useful in medical procedures where there may be advantages to providing real-time soft tissue visualization during an applied therapy.

Figure 3:
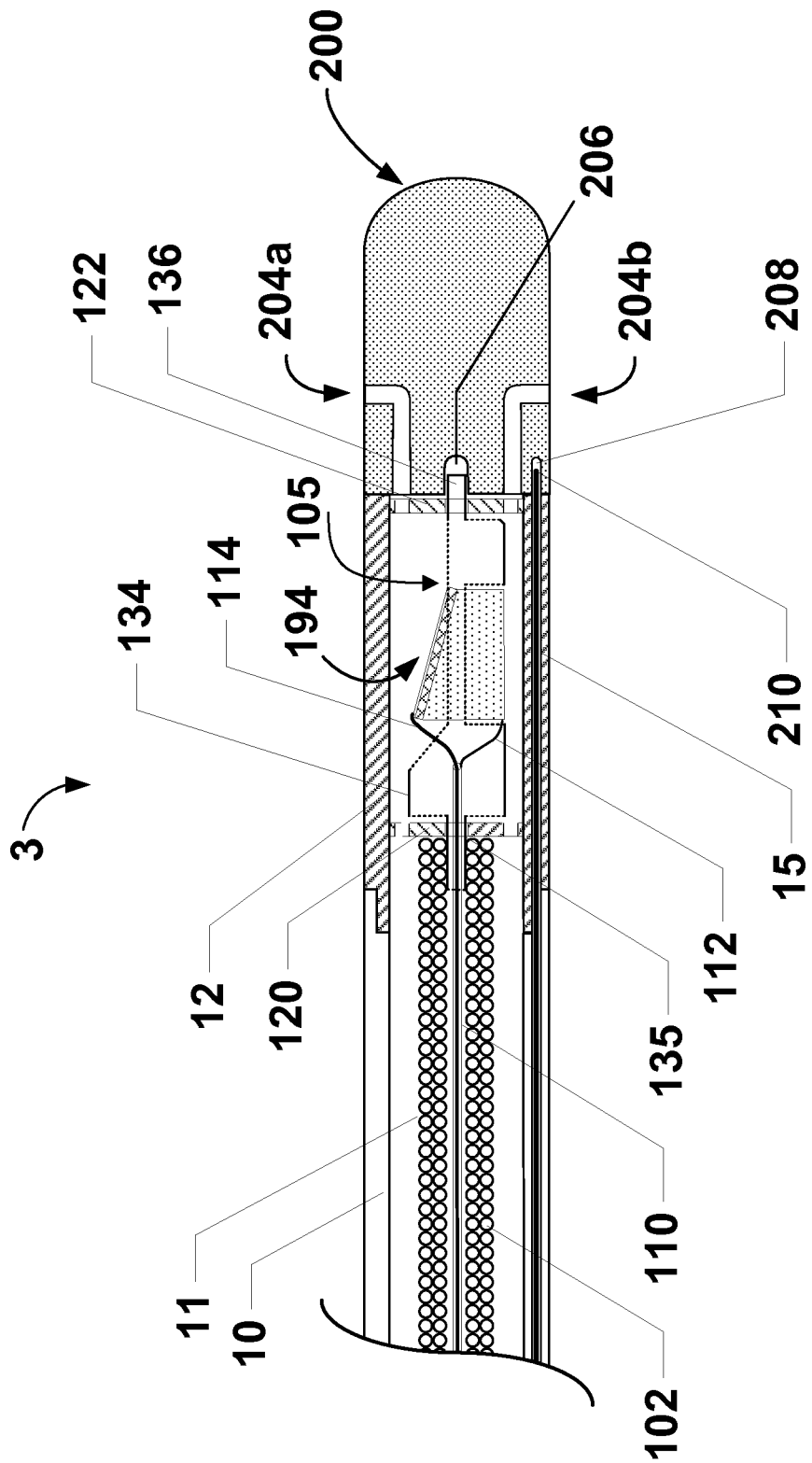
FIG. 3 is a sectional view of an ablation catheter having integrated imaging capabilities in accordance with an embodiment.

FIG. 3 is a sectional view of a radiofrequency (RF) ablation catheter 3 having integrated imaging capabilities in accordance with an embodiment. RF ablation catheter 3 can include midshaft 10, imaging window 12, and distal tip electrode 200. RF ablation catheter 3 can include imaging core lumen 11, lead wire lumen 15, proximal bearing 120, and distal bearing 122. RF ablation catheter 3 may include imaging core 105 wherein imaging core 105 can include torque coil 102, transmission line 110, transducer housing 134, and ultrasound transducer 194.

The length of RF ablation catheter 3 may be generally between 100 cm and 150 cm, more preferably between 110 cm and 120 cm. The outer diameter of the distal section of the RF ablation catheter 3, including imaging window 12 and distal tip electrode 200, may be between 6 F and 10 F.

Distal tip electrode 200 can be designed to ablate cardiac tissue. Distal tip electrode 200 may include an open-irrigation design that can minimize the risk of thrombus formation or blood coagulation. Distal tip electrode 200 may be generally cylindrical in shape. Distal tip electrode 200 may be at least 3 mm in length, more preferably approximately 4 mm. Distal tip electrode 200 may be composed of an electrically conductive material, such as platinum, iridium, stainless steel, or a mixture thereof. Distal tip electrode 200 may include open-irrigation ports 204a, 204b, transducer housing 134, journal hole 206, and lead wire hole 208. Lead wire 210 can be electrically connected to distal tip electrode 200 by bonding to lead wire hole 208 by, for example, soldering or welding. The proximal end of lead wire 210 can be connected to a RF generator that supplies RF energy to the electrode for ablating a lesion in cardiac tissue. Distal tip electrode 200 may include additional open-irrigation ports that may be spaced equidistant around the circumference of the distal tip electrode 200. The catheter may be attached to an irrigation fluid flow system, wherein the irrigation fluid may be saline.

Proximal bearing 120 and distal bearing 122 restrict the longitudinal position of transducer housing 134 and ultrasound transducer 194 with respect to imaging window 12. Transducer housing 134 and ultrasound transducer 194 may be substantially fixed in longitudinal position with respect to imaging window 12 and distal tip electrode 200. The face of ultrasound transducer 194 may be oriented at a non-parallel angle with respect to the catheter axis. The non-parallel angle of the face of ultrasound transducer 194 may ensure that a substantial portion of the tissue to be treated by distal tip electrode 200 is imaged. The angle of ultrasound transducer 194 can be chosen to minimize the travel path of the imaging frequency through the catheter sheath and refraction from the catheter sheath. The angle may also improve image quality by minimizing potential interference that may result from ultrasound energy passing through imaging window 12. The angle can also center the ablative lesion relative to the imaging plane of ultrasound transducer 194 such that a substantial portion of the tissue to be treated is imaged. In one example, the angle can be between 4-10 degrees relative to the catheter axis.

The specific imaging frequency of ultrasound transducer 190 and the ablation frequency of distal tip electrode 200 may be chosen in light of a number of factors. These factors may include minimizing interference to the ultrasound imaging that may be caused by the ablation frequency, increasing the contrast between ablated tissue relative and un-ablated tissue in the ultrasound image, the resolution and depth penetration of the imaging frequency, and so on. These factors may be taken into account when determining the appropriate imaging frequency and ablation frequency for a particular treatment or application.

When RF ablation and ultrasound imaging are performed simultaneously, for example in a RF ablation catheter having integrated imaging capabilities, the RF ablation may interfere with the ultrasound imaging and may cause the ultrasound image to contain a noise pattern or static. The interference may be caused by harmonic frequencies generated by RF ablation. Generally, the extent of the interference may be characterized by the power level of the interference relative to the power level of the imaging frequency. For example, when the power level of the interference caused by the ablating frequency can be 5% of the power level of the imaging frequency, interference to the ultrasound image will be minimal. Conversely, when the power level of the interference can be 95% of the power level of the imaging frequency, there will be substantial interference to the ultrasound image. The difference in power levels between the interference and the imaging frequency may be characterized by decibels (dB). Generally, interference may affect image quality when the power level of the interference caused by the RF ablation can be greater than 50% of the power level of the imaging frequency. In some embodiments, selecting an imaging frequency and an ablation frequency where the power level of the interference from the ablation frequency can be less than 50% of the power level of the imaging frequency may minimize interference to an ultrasound image. In some embodiments, selecting an imaging frequency and an ablation frequency where the power level of the interference from the ablation frequency can be less than 40% of the power level of the imaging frequency may minimize interference to an ultrasound image. In some embodiments, selecting an imaging frequency and an ablation frequency where the power level of the interference from the ablation frequency can be less than 30% of the power level of the imaging frequency may minimize interference to an ultrasound image. In some embodiments, selecting an imaging frequency and an ablation frequency where the power level of the interference from the ablation frequency can be less than 20% of the power level of the imaging frequency may minimize interference to an ultrasound image. In some embodiments, selecting an imaging frequency and an ablation frequency where the power level of the interference from the ablation frequency can be less than 10% of the power level of the imaging frequency may minimize interference to an ultrasound image. In some embodiments, selecting an imaging frequency and an ablation frequency where the power level of the interference from the ablation frequency can be 20-50% of the power level of the imaging frequency may minimize interference to an ultrasound image. In some embodiments, selecting an imaging frequency and an ablation frequency where the power level of the interference from the ablation frequency can be 10-40% of the power level of the imaging frequency may minimize interference to an ultrasound image. In some embodiments, selecting an imaging frequency and an ablation frequency where the power level of the interference from the ablation frequency can be 20-40% of the power level of the imaging frequency may minimize interference to an ultrasound image. In some embodiments, selecting an imaging frequency and an ablation frequency where the power level of the interference from the ablation frequency can be 10-50% of the power level of the imaging frequency may minimize interference to an ultrasound image.

RF ablation is generally performed at a frequency less than or equal to 1 MHz while ultrasound imaging is generally performed between 1-60 MHz. The imaging frequency can be inversely correlated to the extent of interference. As the imaging frequency is increased, the power level of the interference decreases relative to the power level of the imaging frequency. Therefore, performing ultrasound imaging at higher imaging frequencies during RF ablation will produce ultrasound images with less interference than lower imaging frequencies. In some embodiments, configuring an ultrasound transducer to image at a frequency between 10-60 MHz may minimize interference to an ultrasound image. In some embodiments, configuring an ultrasound transducer to image at a frequency between 20-50 MHz may minimize interference to an ultrasound image. In some embodiments, configuring an ultrasound transducer to image at a frequency between 30-40 MHz may minimize interference to an ultrasound image. In some embodiments, configuring an ultrasound transducer to image at a frequency above 10 MHz may minimize interference to an ultrasound image. In some embodiments, configuring an ultrasound transducer to image at a frequency above 20 MHz may minimize interference to an ultrasound image. In some embodiments, configuring an ultrasound transducer to image at a frequency above 30 MHz may minimize interference to an ultrasound image. In some embodiments, configuring an ultrasound transducer to image at a frequency above 40 MHz may minimize interference to an ultrasound image.

A factor to consider when choosing an imaging frequency and ablation frequency is the contrast between ablated tissue and un-ablated tissue in an ultrasound image both during ablation and post-ablation. Ablated tissue and un-ablated tissue may vary in brightness relative to each other in an ultrasound image depending on the imaging frequency. During RF ablation, ablated tissue can generally appear brighter relative to the un-ablated tissue as the RF energy heats the tissue causing the tissue to de-gas. The escaping gas bubbles in the tissue can act as scatters to the ultrasound causing the area to appear brighter in an ultrasound image. As the ablation frequency increases, the rate of de-gassing may also increase which may cause the ultrasound image of the ablation region to become brighter more quickly. After ablation, ablated tissue can generally appear darker relative to un-ablated tissue in an ultrasound image. The difference in brightness, or rather the contrast, between ablated and un-ablated tissue after ablation may increase as the imaging frequency increases. As the imaging frequency is increased, ablated tissue may appear increasingly darker relative to un-ablated tissue. The contrast between ablated and un-ablated tissue both during and after ablation may be considered in choosing the ablation frequency and the imaging frequency. The contrast of the tissues may assist the user of an RF ablation catheter to determine the extent of ablation as well as distinguish treated tissue from untreated tissue.

A factor to consider is having an imaging frequency with the resolution and depth penetration appropriate for a specific application. Higher imaging frequencies enable higher spatial resolution at the expense of depth penetration, while lower imaging frequencies enable depth penetration at the expense of spatial resolution. It can be appreciated that different procedures and treatments may call for a specific spatial resolution or a specific depth penetration.

In consideration of these factors, the imaging frequency and RF ablation frequency may vary depending on the specific treatment or procedure being performed.

Figure 4:
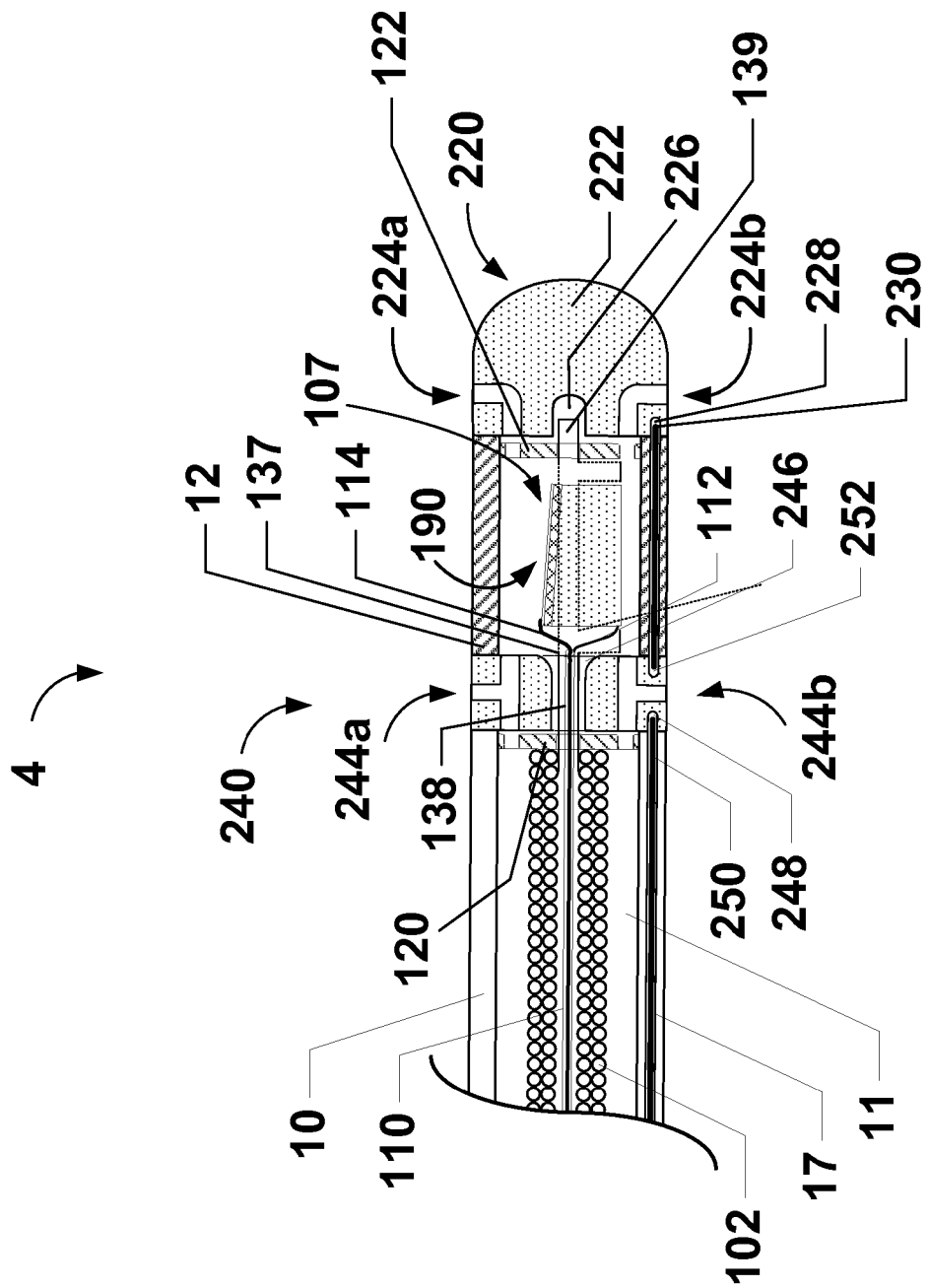
FIG. 4 is a sectional view an ablation catheter having integrated imaging capabilities in accordance with an embodiment.

FIG. 4 is a sectional view of RF ablation catheter 4 having integrated imaging capabilities in accordance with an embodiment. RF ablation catheter 4 can include midshaft 10, imaging window 12, distal electrode 220 and proximal electrode 240. RF ablation catheter 3 can include imaging core lumen 11, first lead wire lumen 17, proximal bearing 120, and distal bearing 122. RF ablation catheter 4 may include imaging core 107 wherein imaging core 107 may include torque coil 102, transmission line 110, transducer housing 137, and ultrasound transducer 190.

Proximal electrode 240 can include open-irrigation channels 244a, 244b, transducer housing journal pass-through channel 246, lead wire hole 248, and connecting wire hole 252. Lead wire 250 can be electrically connected to proximal electrode 240 by bonding to lead wire hole 248 by, for example, soldering or welding. Proximal electrode 240 may include additional open-irrigation channel that may be spaced equidistant around the circumference of proximal electrode 240.

Connecting lead wire 230 electrically connects proximal electrode 240 and distal electrode 220. The electrically connected proximal and distal electrodes 240, 220 may operate as a single distributed electrode. The proximal end of lead wire 250 can be connected to a RF generator that supplies RF energy to the electrically connected proximal and distal electrodes 240, 220 for ablating heart tissue. In another example, RF ablation catheter 4 may have multiple lead wires such that proximal electrode 240 and distal electrode 220 have different lead wires. In such an example, proximal electrode 240 and distal electrode 220 are not electrically connected and may be operated independent of each other. It can be appreciated that RF ablation catheter 4 may have more than two electrodes and the electrodes may or may not be electrically coupled in any combination. RF ablation catheter 4 may have multiple lead wires to each respective electrode such that the electrodes may be controlled in combination or independently in any combination.

As noted above, and illustrated in FIG. 3, the angle of ultrasound transducer 190 can be chosen to minimize the travel path of the imaging frequency through the catheter sheath and refraction from the catheter sheath. The angle may also improve image quality by minimizing potential interference that may result from ultrasound energy passing through imaging window 12. The angle can also center the ablative lesion relative to the imaging plane of ultrasound transducer 190 such that a substantial portion of the tissue to be treated is imaged. For example, the angle can be between 4-10 degrees relative to the catheter axis. In this example, the electrically connected proximal and distal electrodes 240, 220 generate an ablative lesion that is already substantially centered within the imaging plane of ultrasound transducer 190. Consequently, the angle of ultrasound transducer 190 may be configured only to minimize interference that may be caused by distal electrode 220.

Figure 5:
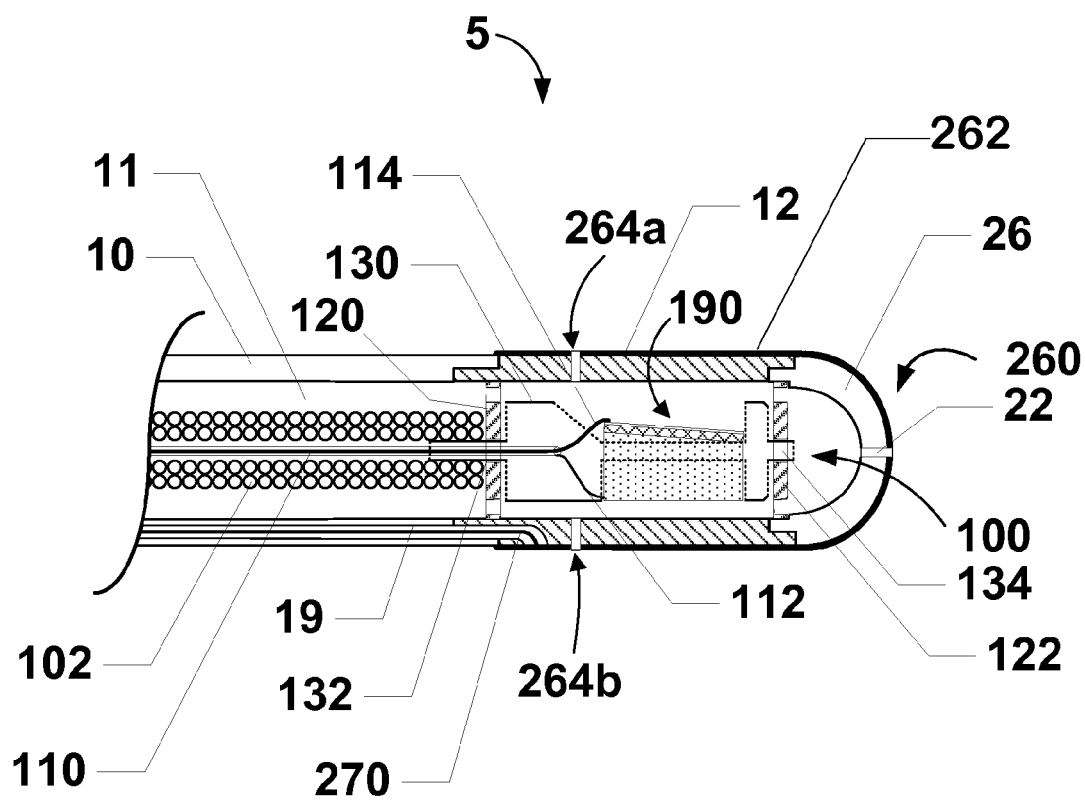
FIG. 5 is a sectional view an ablation catheter having integrated imaging capabilities in accordance with an embodiment.

FIG. 5 is a sectional view of a RF ablation catheter 5 having integrated imaging capabilities in accordance with an embodiment. RF ablation catheter 5 can include midshaft 10, imaging core lumen 11, imaging window 12, distal tip 26, proximal bearing 120, distal bearing 122, and distal tip electrode 260. Distal tip electrode 260 can include a thin electrically conductive layer 262, open-irrigation ports 264a, 264b, and lead wire 270. Distal tip electrode 260 may include additional open-irrigation ports that may be spaced equidistant around the circumference of distal tip electrode 260. RF ablation catheter 5 may include flushing exit port through which a flushing fluid may exit the catheter. The thin electrically conductive layer 262 may be composed of an electrically conductive material, such as platinum, iridium, stainless steel, or a mixture thereof. The thin electrically conductive layer 262 may be machined or laser-cut material and then adhered to imaging window 12 and distal tip 26. Alternatively, the thin electrically conductive layer 262 may be deposited on imaging window 12 and distal tip 26 using vapor deposition methods, such as sputter deposition. The thin electrically conductive layer 262 may be substantially, acoustically transparent. An advantage of a RF ablation catheter having a thin ablation electrode on the imaging window is that an imaging artifact due to an ablation electrode lead wire or connecting wire is avoided.

FIGS. 6 and 6A are sectional views of a steerable ablation catheter 6 having integrated imaging capabilities in accordance with an embodiment. Steerable ablation catheter 6 may include imaging window 12, distal electrode 220, proximal electrode 240, and deflection section 300. Deflection section 300 includes deflection section sheath 302, pull wire lumens 304, 306, reinforcement coil 308, steering ring 310, and pull wires. Deflection section sheath 302 may be formed of a reinforced polymer such as braided polyurethane. The distal ends of pull wires may be bonded to the steering ring 310, typically by welding, brazing, or soldering. The proximal ends of pull wire wires are bonded to a deflection control mechanism that ensures that steerable ablation catheter 6 bends in deflection section 300. An advantage of a RF ablation catheter having a steerable section is that the catheter may be more easily guided to the anatomical site of interest for treatment without need of steerable sheath or other guiding devices.

Figure 7:
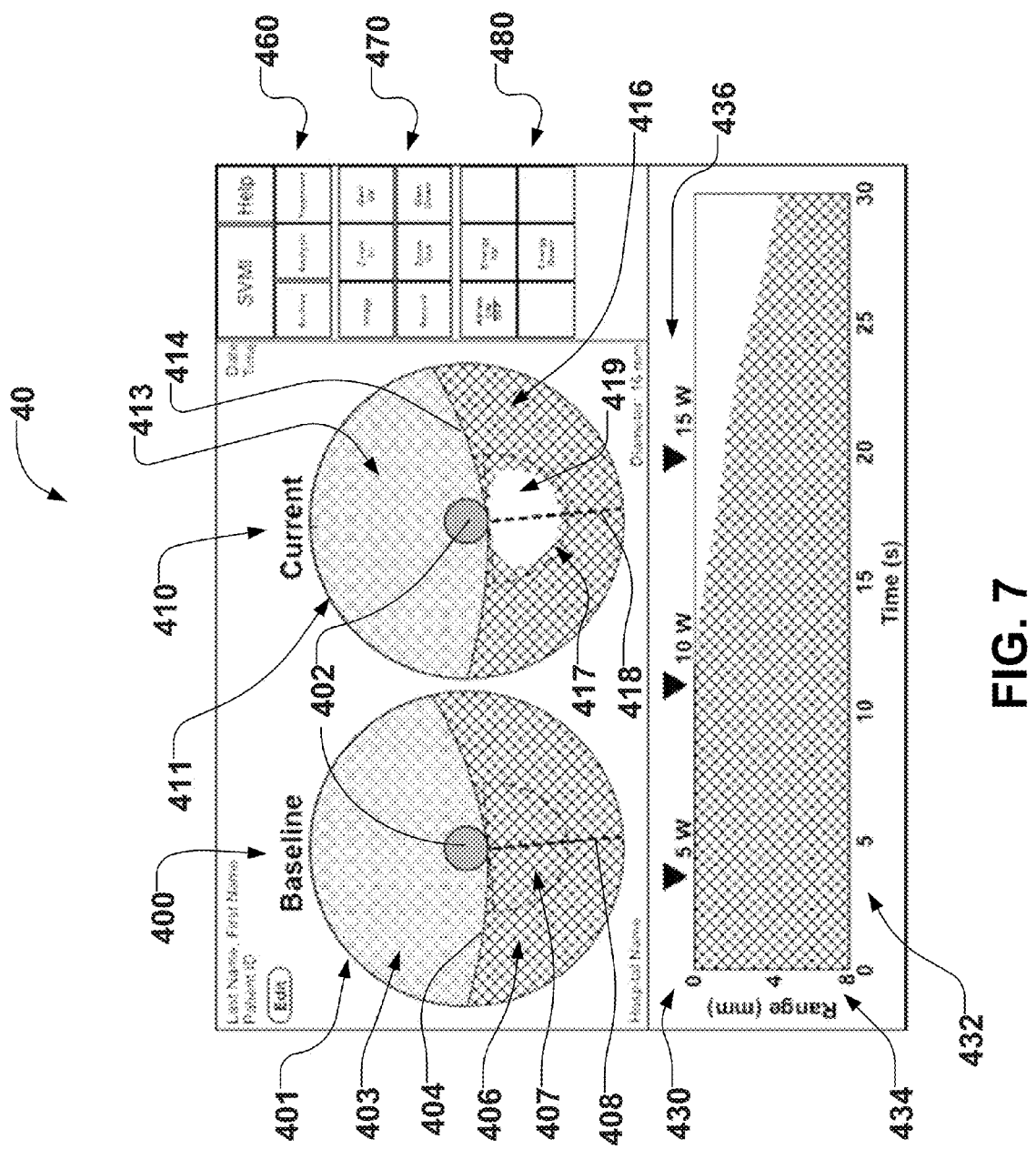
FIG. 7 is a graphical user interface of an imaging console in accordance with an embodiment.

FIG. 7 illustrates a graphical user interface of an imaging console in accordance with an embodiment. In this example, the console can be electrically connected to the imaging core and RF ablator of a catheter by a transmission line and a lead wire, respectively. The console can allow the operator of the catheter to control the ablator and to view images captured by the imaging core. FIG. 7 shows baseline image 400 captured by the imaging core of a catheter of treatment area 401. Treatment area 401 is shown relative to catheter 402 and can include cardiac chamber 403, which is generally filled with blood, and cardiac tissue 406. Catheter 402 is shown to be in contact with endocardial surface 404 of cardiac tissue 406. Baseline image 400 may display a target ablation region 407 (shown as a dashed semicircle). Baseline image 400 may include ablation vector 408 that begins at catheter 402 and extends into cardiac tissue 406 through target ablation region 407. Both target ablation region 407 and ablation vector 408 may be calculated and superimposed on baseline image 400 using a computer processor.

FIG. 7 shows a current image 410 of treatment area 411. Treatment area 411 is shown relative to catheter 402 and can include cardiac chamber 413, cardiac tissue 416, surface 414, target ablation region 417 and ablation vector 418. Current image 410 may include an ablated region 419. Treatment area 411 of current image 410 may correspond with treatment area 401 of baseline image 400. When the treatment areas 401, 411 correspond then their respective cardiac chambers 403, 413, cardiac tissues 406, 416, surfaces 404, 414, target ablation regions 407, 417 and ablation vectors 408, 418 may likewise correspond.

Generally, ablating cardiac tissue damages the tissue, causing it to have different physical properties from normal cardiac tissue. When imaged, damaged cardiac tissue will have a different brightness from normal cardiac tissue. In this example, baseline image 400 is a captured image of treatment area 401 before ablation and current image 410 is a real-time, updated image of corresponding treatment area 411. As shown in FIG. 7, the area of ablated region 419 can have a different brightness in current image 410 compared to the same region in baseline image 400. The user of imaging console 40 may use current image 410 to guide the ablation while using baseline image 400 as a reference to determine the extent of ablation. Generally, baseline image 400 may be useful as a reference to current image 410 when treatment areas 401, 411 correspond.

Imaging console 40 may include a chart 430. Chart 430 can be updated in real-time. In some embodiments, chart 430 may chart any static or real-time metric to assist the user of imaging console 40 in ablating a treatment area. In this example, chart 430 shows the depth of ablation 434 as a function of elapsed time 432, where depth of ablation 434 corresponds with the brightness of cardiac tissue 416 as shown in current image 410 along ablation vector 418. In FIG. 7, chart 430 shows the brightness along ablation vector 418 of current image 410 over a treatment period of 30 seconds. After 5 seconds of ablation, there was no change in brightness along ablation vector 418. After 20 seconds of ablation, the change in brightness along ablation vector 418 occurs to a depth of approximately 2 mm. After 30 seconds of ablation, the change in brightness along ablation vector 418 occurs to a depth of approximately 4 mm. The brightness of ablation vector 418 after 30 seconds is the last data point and therefore corresponds with the contrast along ablation vector 418 as shown in current image 410. In this example, catheter 402 may include an RF ablator, so chart 430 shows the power 436 of the ablator as a function of time. Chart 430 may assist the user of imaging console 40 in treating treatment area 411 by showing the rate of ablation over time. As noted above, chart 430 is not limited in the type of data it can display. It can be appreciated that the data of chart 430 may be changed to be relevant to different treatment areas, ablators, or imaging cores.

FIG. 7 shows interface including a plurality of selectable icons. Interface may be used by the user to control the imaging core and ablator of catheter 402 as well as the display of imaging console 40. In this example, the selectable icons are divided into three groups of icons 460, 470, 480. The first group of icons 460 may include icons relevant to controlling the imaging console 40, the second group of icons 470 may include icons relevant to controlling the imaging core of catheter 402, and the third group of icons 480 may include icons relevant to controlling the ablator of catheter. It can be appreciated that the icons and their respective functions as well as the grouping of the icons may vary or be configurable for different users, treatments and equipment.

Thus, embodiments of the invention are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention and the scope of the appended claims.

What is claimed is:

1. An ultrasound catheter comprising:
    an elongated body, the elongated body having a longitudinal dimension, a distal end and an imaging core lumen;
    an imaging core disposed within the imaging core lumen and having a transducer housing comprising an ultrasound transducer, wherein the transducer housing comprises a first journal and a second journal;
    a first bearing fixed to the elongated body proximal to the ultrasound transducer;
    a second bearing fixed to the elongated body distal to the ultrasound transducer and configured to receive the second journal, wherein the first and second bearings are configured to restrict longitudinal displacement of the ultrasound transducer within the elongated body and to facilitate 360° rotation of the ultrasound transducer within the imaging core lumen; and
    a first ablation element configured to interface with the second bearing and ablate tissue, wherein the first ablation element defines an aperture having an inner diameter that is less than that of the imaging core lumen to receive the second journal.

2. The catheter of claim 1, wherein the ultrasound transducer rotates relative to the elongated body.

3. The catheter of claim 1, wherein the imaging core further includes a mirror, the mirror being rotatable relative to the elongated body.

4. The catheter of claim 1, wherein the imaging core and the first ablation element are configured such that a treatment area imaged by the imaging core includes the tissue to be ablated.

5. The catheter of claim 1, wherein the first ablation element is a radio frequency ablation element, the first ablation element comprising a first electrode.

6. The catheter of claim 1, wherein
    (a) the ultrasound transducer is configured to generate an imaging signal to image at (i) an imaging frequency greater than or equal to 10 MHz and (ii) an imaging power level,
    (b) the first electrode is configured to ablate at an ablating frequency less than or equal to 1 MHz,
    (c) the first electrode generates an interference signal during ablation having (i) an interference frequency that interferes with the ultrasound transducer when imaging at the imaging frequency and (ii) an interference power level, and
    (d) the interference power level is less than or equal to 50% of the imaging power level.

7. The catheter of claim 1, wherein the first electrode comprises a solid piece of conductive material.

8. The catheter of claim 1, wherein the second bearing defines a channel to facilitate pass-through flow of a fluid, and wherein the first ablation element defines an irrigation port in fluid communication with the channel of the second bearing, the irrigation port extending from the imaging core lumen to an outlet defined at an outer surface of the first ablation element, the outlet defined at a location on the outer surface of the first ablation element proximal to a distal tip of the first ablation element.

9. The catheter of claim 1, wherein the elongated body further includes a deflection section to enable steering of the distal end of the elongated body.

10. The catheter of claim 1, further comprising:
    a torque coil bonded to the first journal and configured to rotate the ultrasound transducer; and
    a transmission line disposed within the torque coil and electrically coupled to the ultrasound transducer.

11. The catheter of claim 10, wherein the transmission line is configured to be rotationally fixed during rotation of the ultrasound transducer.

12. The catheter of claim 8, further comprising:
    a second ablation element configured to interface with the first bearing and ablate soft tissue, wherein the second ablation element defines an aperture to receive the first journal.

13. The catheter of claim 12, wherein the first bearing defines a channel to facilitate pass-through flow of a fluid and the second ablation element defines an irrigation port in fluid communication with the channel of the first bearing, and wherein the first bearing channel and second ablation element irrigation port are in fluid communication with the second bearing channel and first ablation element irrigation port.

14. The catheter of claim 12, wherein the imaging core and the first and second ablation elements are configured such that a treatment area imaged by the imaging core includes the tissue to be ablated by both the first and second ablation elements.

15. The catheter of claim 14, further comprising:
    an imaging window included along the elongated body having first and second opposite longitudinal ends, wherein a side of the first ablation element interfaces with the first longitudinal end of the imaging window and the second bearing, and wherein a side of the second ablation element interfaces with the second longitudinal end of the imaging window and the first bearing.

16. The catheter of claim 12, wherein the first and second ablation elements are radio frequency ablation elements, the first and second ablation elements comprising first and second electrodes respectively, and wherein the first and second electrodes are not electrically coupled to one another and may be independently controlled.

17. An ultrasound catheter comprising:
an elongated body defining an imaging core lumen at a distal portion of the elongated body;
an imaging window included along at least a portion of the distal portion of the elongated body;
an imaging core disposed within the imaging core lumen and having a transducer housing, the transducer housing disposed at a longitudinal location of the imaging window and including an ultrasound transducer and a journal;
a first bearing fixed to the elongated body proximal to the ultrasound transducer;
a second bearing fixed to the elongated body distal to the ultrasound transducer and defining a channel to facilitate pass-through flow of a fluid, wherein the second bearing is configured to receive the journal, and wherein the first and second bearings are configured to restrict longitudinal displacement of the ultrasound transducer within the elongated body; and
a first ablation element disposed distal to the ultrasound transducer and configured to interface with the second bearing, wherein the first ablation element defines a port in fluid communication with the channel of the second bearing, and wherein the first ablation element defines an aperture having an inner diameter that is less than that of the imaging core lumen to receive the second journal.

18. The catheter of claim 17, further comprising a second ablation element, wherein the second ablation element has first and second opposite sides, wherein the second ablation element interfaces with the first bearing on the first side and the transducer housing on the second side.

19. The catheter of claim 17, further comprising:
a deflection section with a deflection sheath included at the distal portion, the deflection sheath defining a pull wire lumen therethrough;
a steering ring disposed within the deflection sheath and proximal to the first bearing;
a pull wire extending through the pull wire lumen, wherein a distal end of the pull wire is coupled to the steering ring and a proximal end of the pull wire is coupled to a deflection control mechanism.

20. The catheter of claim 1, wherein the ultrasound transducer has a face oriented at an angle between 4 and 10 degrees with respect to a central longitudinal axis of the catheter.

21. The catheter of claim 13, wherein the aperture defined by the second ablation element has an inner diameter that is less than that of the imaging core lumen, and wherein the irrigation port of the second ablation element is defined at an outer surface of the second ablation element.

22. The catheter of claim 17, wherein the port is in fluid communication with the channel on a first end and an outlet defined at an outer surface of the first ablation element on a second opposite end.

23. The catheter of claim 17, wherein the first bearing defines a channel to facilitate pass-through flow of the fluid, and wherein the channel of the first bearing is in fluid communication with the channel of the second bearing and the port of the first ablation element.

24. An ultrasound catheter comprising:
an elongated body, the elongated body having a longitudinal dimension, a distal end and an imaging core lumen;
an imaging core disposed within the imaging core lumen and having a transducer housing comprising an ultrasound transducer and a journal;
a first bearing fixed to the elongated body proximal to the ultrasound transducer;
a second bearing fixed to the elongated body distal to the ultrasound transducer and configured to receive the journal, wherein the first and second bearings are configured to restrict longitudinal displacement of the ultrasound transducer within the elongated body; and
a first ablation element configured to interface with the second bearing, wherein the first ablation element defines an aperture having an inner diameter that is less than that of the imaging core lumen to receive the journal.

25. The catheter of claim 24, wherein the imaging core and the first ablation element are configured such that a treatment area imaged by the imaging core includes the tissue to be ablated.

26. The catheter of claim 24, further comprising:
a second ablation element configured to interface with the first bearing.

27. The catheter of claim 26, wherein the transducer housing comprises a second journal, and wherein the second ablation element defines an aperture to receive the second journal .

28. The catheter of claim 27, wherein the aperture of the second ablation element has an inner diameter that is less than that of the imaging core lumen.

29. The catheter of claim 26, further comprising:
an imaging window included along the elongated body having first and second opposite longitudinal ends, wherein a side of the first ablation element interfaces with the first longitudinal end of the imaging window and the second bearing, and wherein a side of the second ablation element interfaces with the second longitudinal end of the imaging window and the first bearing.

30. The catheter of claim 24, wherein the ultrasound transducer has a face oriented at an angle between 4 and 10 degrees with respect to a central longitudinal axis of the catheter.

* * * * *